(12) United States Patent
Skarky

(10) Patent No.: US 6,979,195 B2
(45) Date of Patent: Dec. 27, 2005

(54) DENTAL DEVICE FOR FORMING A DENTAL APPLIANCE WHICH POSITIONS THE MANDIBLE AND THE MAXILLA IN CENTRIC RELATION AND METHODS FOR USING SAME

(76) Inventor: Floyd E. Skarky, 6305 Waterford Blvd., Ste. 445, Oklahoma City, OK (US) 73118

( * ) Notice: Subject to any disclaimer, the term of this patent is extended or adjusted under 35 U.S.C. 154(b) by 0 days.

(21) Appl. No.: 10/703,366

(22) Filed: Nov. 7, 2003

(65) Prior Publication Data

US 2005/0100857 A1    May 12, 2005

(51) Int. Cl.⁷ ............................................... A61C 9/00
(52) U.S. Cl. ........................................ 433/71; 433/34
(58) Field of Search .......................... 433/34, 37, 45, 433/47, 71

(56) References Cited

U.S. PATENT DOCUMENTS

| | | | |
|---|---|---|---|
| 2,694,397 A | 11/1954 | Herms | 128/861 |
| 2,833,278 A | 5/1958 | Ross | 128/862 |
| 3,478,429 A | 11/1969 | Shilliday | 433/6 |
| 3,532,091 A | 10/1970 | Lerman | 128/862 |
| 4,211,008 A | 7/1980 | Lerman | 433/6 |
| 4,445,856 A | 5/1984 | Strurtzkopf | 433/71 |
| 4,543,062 A * | 9/1985 | Lee | 433/71 |
| 4,624,640 A | 11/1986 | Tesini | 433/71 |
| 4,676,748 A | 6/1987 | Pietkivitch | 433/71 |
| 5,082,007 A | 1/1992 | Adell | 128/861 |
| 5,293,880 A | 3/1994 | Levitt | 128/861 |
| 5,513,656 A | 5/1996 | Boyd, Sr. | 433/6 |
| 6,135,768 A | 10/2000 | Skarky | 433/71 |
| 6,231,339 B1 | 5/2001 | Skarky | 433/71 |

OTHER PUBLICATIONS

Evaluation, Diagnosis and Treatment of Occlusal Problems, by Peter Dawson, Second Edition, Copyright 1989, pp. 36, 37, 41, 42, 43, 44, 45, 46, 47, 168, 169, 170, 171, 172, 189, 190, 191, 192, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237.

Exhibit A is a photograph of a leaf gage which has been used by dentists in the past for attempting to position the maxilla and the mandible in centric relation.

Exhibit B is a photograph of a device having two different hardnesses of wax; has also been used in the past in an attempt to establish centric relation between the maxilla and the mandible.

Exhibit C is a photograph of a Lucia Jig which was a cap-like structure which was fitted over the upper and lower anterior teeth.

* cited by examiner

*Primary Examiner*—Cary E. O'Connor
(74) *Attorney, Agent, or Firm*—Dunlap, Codding and Rogers P.C.

(57) ABSTRACT

The present invention relates generally to dental devices, and more particularly, but not by way of limitation, to a dental device for forming a dental appliance. The dental appliance is used to position the mandible and the maxilla in centric relation and methods of making and using same.

18 Claims, 3 Drawing Sheets

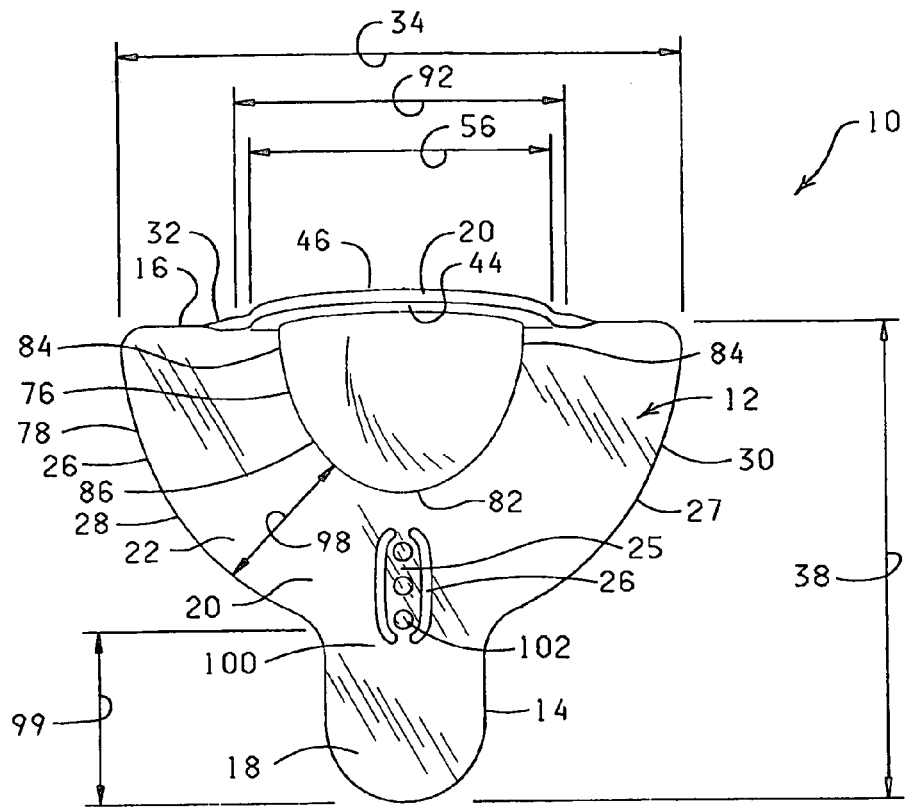
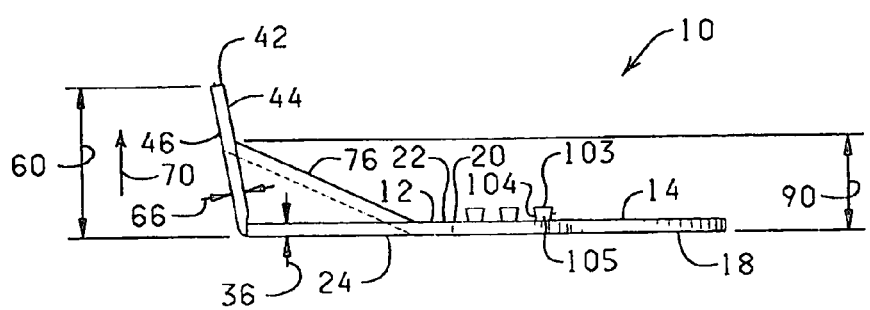

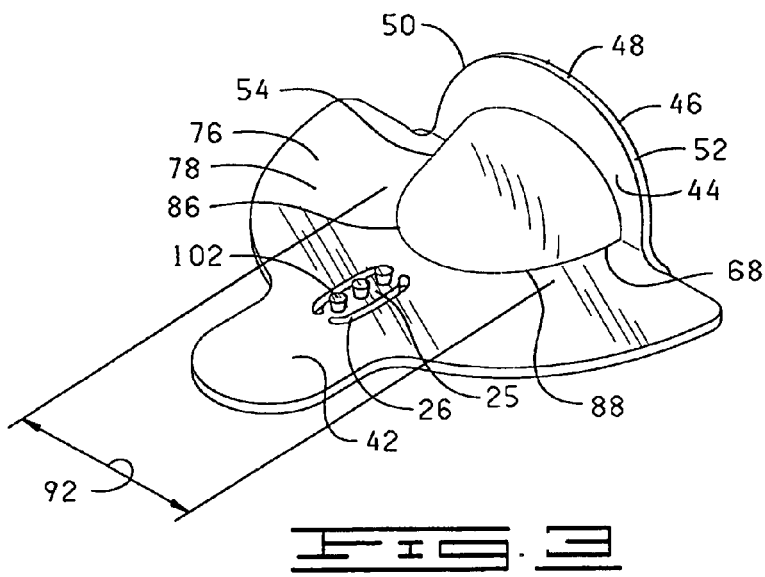
___Fig. 3___
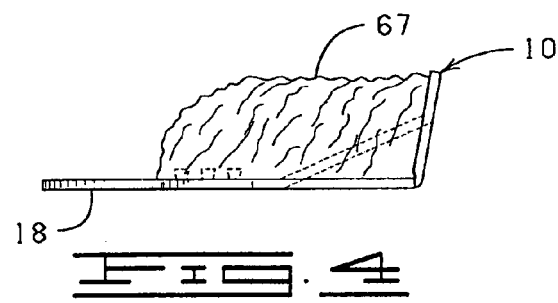
___Fig. 4___
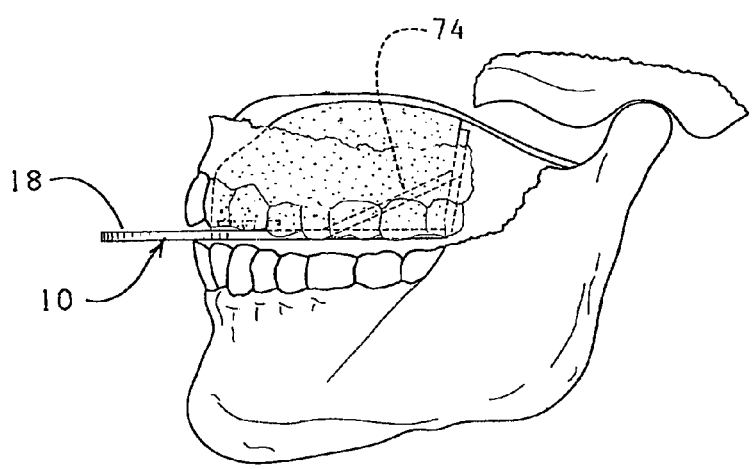
___Fig. 5___

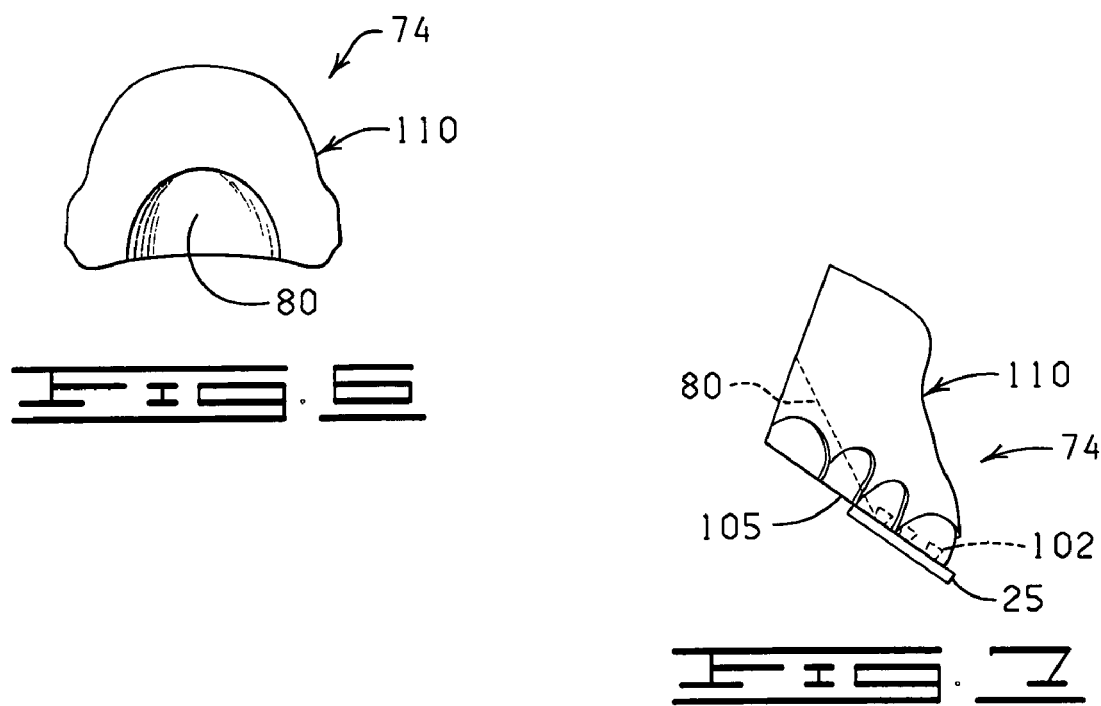
FIG. 6
FIG. 7
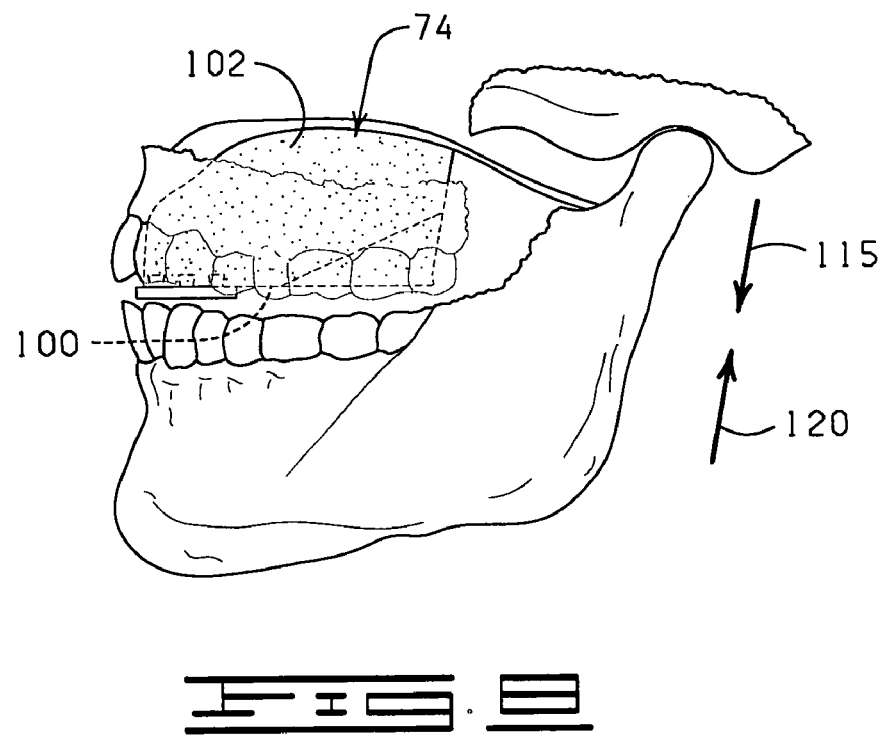
FIG. 8

DENTAL DEVICE FOR FORMING A DENTAL APPLIANCE WHICH POSITIONS THE MANDIBLE AND THE MAXILLA IN CENTRIC RELATION AND METHODS FOR USING SAME

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

FIeld of the Invention

The present invention relates generally to dental devices, and more particularly, but not by way of limitation, to a dental device for forming a dental appliance and methods of making and using the dental device and the dental appliance. The dental appliance is typically used to position the mandible and the maxilla in centric relation.

BRIEF DESCRIPTION OF THE SEVERAL VIEWS OF THE DRAWING

FIG. 1 is a top plan view of a dental device constructed in accordance with the present invention.

FIG. 2 is a side view of the dental device of FIG. 1.

FIG. 3 is a perspective view of the dental device of FIGS. 1 and 2.

FIG. 4 is a side view of the dental device with a rapid setting impression material disposed thereon.

FIG. 5 is a partial cutaway side view showing the dental device disposed between the upper and lower teeth of a patient with a rapid setting impression material disposed on the dental device with the patient's mandible and maxilla in centric relation.

FIG. 6 is a top plan view of a dental appliance formed from the rapid setting impression material after removal from the dental device.

FIG. 7 is a perspective view of the dental appliance formed with the assistance of the dental device.

FIG. 8 is a diagrammatic, schematic view showing a portion of a maxilla and a portion of a mandible with the dental appliance of FIGS. 6 and 7 inserted between the upper and the lower teeth with the upper and the lower teeth shown in a closed position and the mandible and the maxilla in centric relation.

DETAILED DESCRIPTION OF THE DRAWINGS

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for purpose of description and should not be regarded as limiting.

Referring now to FIGS. 1–3 shown therein and designated by the general reference numeral 10 is a dental device constructed in accordance with the present invention. The dental device 10 is constructed of materials adapted, sized and shaped so as to be inserted into a patient's mouth between the patient's upper teeth and lower teeth. Typically, the dental device 10 is formed from a substantially rigid plexiglass type material, however, the device can be constructed from any non-toxic, strong, and rigid material capable of being formed into the shape of the dental device 10 such as metal, ceramic, plastic or derivations and combinations thereof.

The term "centric relation" as used herein means that when the mandible and the maxilla are properly aligned, condyle-disk assemblies are in the most superior position against the eminentia, irrespective of tooth position or vertical dimension. In this position, the head of the condyle of the mandible is in the upper most superior position in the glenoid fossa with a disk assembly between it and the eminentia. The term "centric relation" is well known to those skilled in the art of dentistry, and a more detailed description or illustrations are not deemed necessary as the plain meaning would be apparent to one of ordinary skill in the art.

An individual patient has two sets of muscles that control centric relation, a set of elevator muscles and a set of positioner muscles. The elevator muscles are the masseter, temporalis, medial pterygoid and the positioner muscles are the lateral pterygoid, and anterior fibers of the temporalis. When one set of muscles fires, the other set of muscles should release. That is, when the elevator muscles fire, the positioner muscles release, and when the positioner muscles fire, the elevator muscles release. When this does not occur the muscles of the masticatory system do not coordinate thereby causing isometric contraction, pain and destruction of the dentition.

The dental device 10 includes an impression support platform 12, having a front end 14 and a back end 16, a tab 18 extending outward from the front end 14 of the impression support platform 12 and a dam 20 extending substantially upwardly from the back end 16 of the impression support platform 12. The impression support platform 12 is sized and shaped so as to be disposed between the patient's upper anterior teeth and the patient's lower anterior teeth.

The impression support platform 12 has an upper surface 22, a lower surface 24, a detachable central portion 25 at least one detaching element 26 for detaching the detachable central portion 25 from the impression support platform 12 and a substantially semi-circular outer periphery 27. The substantially semi-circular outer periphery 27 has an first side 28, an second side 30 and a rear edge 32. The impression support platform 12 also has a maximum width 34 defined by the distance along the rear edge 32 from the first side 28 to the second side 30, a thickness 36 defined by the distance from the upper surface 22 to the lower surface 24 and a length 38. The length 38 and maximum width 34 of the impression support platform 12 is such that the first side 28 and the second side 30 extend a small distance beyond a buccal edge of the patient's upper teeth. The thickness 36 of the impression support platform 12 and the rigidity of impression support platform 12 are such that the patient's upper teeth are maintained in a spaced apart configuration from the patient's lower teeth when the patient bites down on the detachable central portion 25 of the impression support platform 12.

The dam 20 has a front surface 44, a back surface 46 and a substantially semi-circular outer periphery 48. The substantially semi-circular outer periphery 48 has an arcuate left side 50, an arcuate right side 52 and a lower edge 54. The dam 20 also has a maximum width 56, a height 60 (FIG. 2), and a thickness 66 (FIG. 2). The dam 20 is sized and shaped such that dam 20 fits within the patient's mouth, and the dam 20 blocks a rapid setting impression material 67 (shown in FIG. 4 and described in more detail hereinafter) disposed on the upper surface 22 of the impression support platform 12 from going down the patient's throat when placed in the patient's mouth. The thickness 66 of the dam 20 is defined by the distance from the front surface 44 of the dam 20 to the back surface 46 of the dam 20.

The maximum width 56 of the dam 20 is typically less than the maximum width 34 of the impression support platform 12. The lower edge 54 of the dam 20 is joined to at least a central portion 68 of the rear edge 32 of the impression support platform 12 such that the front surface 44 of the dam 20 extends in a perpendicular upwardly direction 70 from the upper surface 22 of the impression support platform 12. When the patient's mouth is closed around the dental device 10, the upper surface 22 of the impression support platform 12, the front surface 44 of the dam 20, the patient's upper anterior teeth, and the patient's palate substantially enclose and define a mold 72 (FIG. 5) for molding a dental appliance 74 (FIGS. 6 and 7). When the dental device 10 is disposed into the patient's mouth the lower anterior teeth contact the lower surface 24 of the impression support platform 12 and as the patient closes their mouth the dental device 10 is moved in a direction upwardly toward the palate and upper anterior teeth of the patient.

The upper surface 22 of the impression support platform 12 has a convex section 76 and a planar section 78. The convex section 76 provides the dental appliance 74 (FIGS. 6 and 7) with an air passageway 80 (FIGS. 6 and 7). The planar section 78 extends inwardly along the first side 28 and the second side 30 of the substantially semi-circular outer periphery 27 of the impression support platform 12. The planar section 78 and the impression support platform 12 supports the rapid setting impression material 67 when the rapid impression material 67 is disposed thereon. An example of the rapid setting impression material 67 which can be used in the practice of the present invention is of the type generally referred to as BLU-MOUSSE and is commercially available from Parkell Products, Inc., New York. The convex section 76 is centrally disposed on the upper surface 22 of the impression support platform 12 equal distance from the first side 28 and the second side 30 of the impression support platform 12. The convex section 76 has a front 82 and a back 84. The front 82 of the convex section 76 is nearest to the tab 18 of the impression support platform 12. The back 84 of the convex section 76 abuts the front surface 44 of the dam 20. The convex section 76 tapers from a maximum height above the planar section 78 at the back 84 of the convex section 76 to a minimum height above the planar section 78 at the front 82 of the convex section 76. The back 84 of the convex section 76 has an arcuate first side 86, an arcuate second side 88, a maximum height 90 and a maximum width 92. The maximum height 90 of the convex section 76 is typically equal to or lesser than the height 60 of the dam 20 and the maximum width 92 of the convex section 76 is typically equal to or lesser than the maximum width 56 of the dam 20. The convex section 76 is typically sized and shaped to be substantially defined by the interior of the patient's mouth being bound by the interior of the perimeter of the patient's teeth, the patient's palate, and the upper surface 22 of the impression support platform 12.

The planar section 78 of the upper surface 22 of the impression support platform 12 has a width 98 that is substantially uniform and which generally extends inwardly from the substantially semi-circular outer periphery 27 of the impression support platform 12 toward the convex section 76. The width 98 of the planar section 78 of the upper surface 22 of the impression support platform 12 is at least sufficient to accommodate the width of the patient's teeth although it should be noted that typically the width 98 of the planar section 78 is sufficient so as to extend at least a short distance outwardly past the outer perimeter of the patient's upper and lower teeth. It should also be noted that although the impression support platform 12 is described and shown herein has having the substantially semi-circular outer perimeter 27, can instead be linear, non-linear, angular or even fanciful as long as the width 98 of the planar section 78 of the upper surface 22 of the impression support platform 12 is sufficient to at least accommodate the patient's teeth and preferably extend a short distance outwardly from the outer perimeter of the patient's upper and lower teeth.

The tab 18 extends a distance 99 away from an apex 100 of the impression support platform 12. The tab 18 can be coplanar with the impression support platform 12 or the tab 18 can extend away from the impression support platform in an angularly upwardly or downwardly manner from the impression support platform 12. The tab 18 is adapted to be gripped by an individual (such as the dentist or patient) to allow for the insertion and positioning of the dental device 10 in a patient's mouth, as will be described in greater detail herein below.

The detachable central portion 25 of the impression support platform 12 is designed to detach from the impression support platform 12 and remain embedded in or attached to the dental appliance 74 after the rapid setting impression material 67 has hardened and the dental appliance 74 has been formed. The detachable central portion 25 of the impression support platform 12 is intended to discourage the patient from chewing on and thereby deforming the dental appliance 74 when in use. The detachable central portion 25 is also intended to provide that only a central portion of the patient's lower teeth contact the dental appliance 74 when the patient bites down on the dental appliance 74.

The detachable central portion 25 of the impression support platform 12 is typically disposed in the planar section 78 of the impression support platform 12 between the front 82 of the convex section 76 and the tab 18. The at least one detaching element 26 typically substantially surrounds the detachable central portion 25. The at least one detaching element is for facilitating detachment of the detachable central portion 25 from the impression support platform 12. The at least one detaching element 26 can be by way of example, but not limitation, a plurality of perforations, a score line, connectors, or combinations and derivations thereof. The detachable central portion 25 includes at least one protuberant 102 designed to facilitate adherence of the detachable central portion 17 to the dental appliance 74. The at least one protuberant 102 extends upwardly from the detachable central portion 25. The at least one protuberant 102 is sized, shaped and designed such that the rapid setting impression material 67 disposed on the upper surface 22 of the impression support platform 12 in its softened condition substantially flows around the at least one protuberant 102 and enhances the attachment of the detachable central portion 25 to the dental appliance 74 as the rapid setting impression material 67 hardens. The at least one protuberant 102 has a top 103, an under cut portion 104 and a bottom 105. The under cut portion 104 provides that the top 103 is larger in area than the bottom 105, thereby further enhancing the attachment of the detachable central portion 25 to the dental appliance 74 when the rapid setting impression material 67 hardens around the at least one protuberant 102.

In one preferred embodiment, the impression support platform 12 is shaped and sized so as to engage substantially from one bicuspid to the other bicuspid. It should be noted that the impression support platform 12 may engage only the incisors and the intervening teeth or the impression support platform 12 also could engage the lateral incisors and still perform the functions of the dental device 10 as described herein.

Referring now to FIG. 4, in forming the dental appliance 74, the dentist disposes a sufficient amount of the rapid setting impression material 67 in a softened condition onto at least the planar section 78 of the upper surface 22 of the impression support platform 12 to flow around the at least one protuberant 102 and at least fill the mold 72 for molding the dental appliance 74.

Referring now to FIG. 5, the dentist grips the tab 18 and, while holding the tab 18, the dentist inserts the dental device 10 with the rapid setting impression material 67 thereon into the patient's mouth between the upper and the lower teeth to a position wherein the planar section 78 of the upper surface 22 of the impression support platform 12 is disposed between at least some of the upper and the lower anterior teeth of the patient and the convex section 76 of the upper surface 22 of the impression support platform 12 is disposed in close proximity to the patient's palate. The dental device 10 and rapid setting impression material 67 are positioned in the patient's mouth such that the upper surface 22 of the impression support platform 12 and the rapid setting impression material 67 disposed thereon are interposed between the upper surface 22 of the impression support platform of the dental device 10 and the patient's palate. The patient then bites down on the dental device 10 or the dental device 10 can be held in position by the dentist or patient.

The patient is typically directed to at least partially close the patient's mouth such that the lower anterior teeth of the patient moves the dental device 10 and rapid setting impression material 67 thereon upwardly in the direction of the patient's palate. The patient maintains this motion until a sufficiently tight seal is affected between the dental device 10 and the patient's palate and upper anterior teeth to form the rapid setting impression material 67 into the dental appliance 74 shown in FIG. 5. The patient maintains this position until the rapid impression material 67 at least partially solidifies. The dental appliance 74 is formed by the rapid setting impression material 67 disposed between the dental device 10, the patient's palate and the patient's upper anterior teeth. In other words, with the dental device 10 properly positioned in the patient's mouth, the dental device 10, the patient's palate and the patient's upper anterior teeth constitute the mold 72 for molding the dental appliance 74.

The dental appliance 74, formed by the dental device 10, is designed to program the upper and the lower arches back to their original position and not to the displaced position. That is, the dental appliance 74 is adapted to cooperate in positioning the mandible and the maxilla in centric relation.

After the rapid setting impression material 67 at least partially solidifies, the mouth of the patient is opened. The dental device 10 and dental appliance 74 formed thereby are removed from the patient's mouth. The detachable central portion 25 of the impression support platform 12 is detached from the impression support platform 12 by utilizing the at least one detaching element 26, and/or an appropriate tool in such a manner that the detachable central portion 25 remains embedded in and attached to the dental appliance 74.

Although the exact size and shape of the dental appliance 74 will vary from patient to patient referring now to FIGS. 6 and 7, generally, the dental appliance 74 has: (1) a lower surface 105 which is substantially planar and formed by the substantially planar section 78 of the upper surface 22 of the impression support platform 12 of the dental device 10; (2) the air passageway 80 substantially formed by the convex section 76 of the upper surface 22 of the impression support platform 12 of the dental device 10; (3) a substantially semi-spherical body 110 formed at least, in part, by the patient's palate and upper anterior teeth, and (4) the detachable central portion 25 detached from the impression support platform 12 and substantially embedded in the lower surface 105 of the dental appliance 74.

Referring now to FIG. 8, the dental appliance 74 is useful in at least three different applications, such as, relieving muscle trismus and pain, diagnosing temporal mandibular joint problems and disposing the maxilla and mandible centric relation for recording. To relieve muscle trismus and pain with the patient's mouth in the open position, the dental appliance 74 is positioned between at least some of the patient's lower anterior teeth and palate. The patient then bites down on the dental appliance 74 with the central portion of the patient's lower teeth engaging the detachable central portion 25 embedded in the lower surface 105 of the dental appliance 74 which positions the substantially semi-spherical body 110 of the dental appliance 74 against the patient's palate and continued biting provides forces in the directions 115 and 120 on the dental appliance 74. As the patient bites down on the detachable central portion 25 embedded in the dental appliance 74 and as this position is maintained for a period of time, the mandible and the maxilla are moved into centric relation in the manner described hereinabove with the elevator muscles contracting and the positioner muscles relaxing. In this position, pain caused by the muscles, subsides.

Also, as mentioned hereinabove, the dental appliance 74 is useful in diagnosing temporal mandibular joint problems. With this procedure, the dental appliance 74 is positioned in the patient's mouth in the manner described before wherein the substantially semi-spherical body 110 is fitted substantially against the patient's palate and upper anterior teeth and the lower surface 105 of the dental appliance 74 is disposed in proximity to the patient's lower anterior teeth. In this position, the patient bites down on the detachable central portion 25 embedded in the dental appliance 74 as hard as possible. While the patient bites down on the detachable central portion 25 of the dental appliance 74 if the disk has been displaced forward, the head of the condyle will be compressing the distal ligament, nerve endings and blood vessels against the eminences causing pain. Thus, the dentist can determine that it is a displaced disk causing the problem and it is not a muscle problem. On the other hand, if the disk is between the head of the condyle and eminence and the biting down causes no pain, the dentist knows it is a muscle problem.

Also, as mentioned before, the dental appliance 74 is useful disposing the mandible and maxilla in centric relation in order to record centric relation. With this procedure, the dental appliance 74 is positioned in the patient's mouth in the manner described before wherein the substantially semi-spherical body 110 is fitted substantially against the patient's palate and upper anterior teeth and the lower surface 105 of the dental appliance 74 is positioned against at least some of the patient's lower anterior teeth. As the patient bites down on the detachable central portion 25 embedded in the dental appliance 74 and as this position is maintained for a period of time, the mandible and the maxilla are moved into centric relation in the manner described hereinabove with the elevator muscles contracting and the positioner muscles relaxing.

In order to record centric relation, after the mandible and the maxilla are positioned in centric relation as described above. The dentist can utilize a system such as the system described in U.S. Pat. No. 6,231,339, the contents of which is expressly incorporated herein in its entirety by reference, in a manner described therein, to record the centric relation of the patient's mandible and maxilla.

Changes may be made in the construction and the operation of the various components, elements and assemblies described herein and changes may be made in the steps or the sequence of steps of the methods described herein without departing from the spirit and scope of the invention as defined in the following claims.

What is claimed is:

1. A method of forming a dental appliance for positioning a patient's mandible and maxilla in centric relation, the method comprising the steps of:
   providing a rapid setting impression material;
   providing a dental device comprising:
      an impression support platform for supporting the rapid setting impression material, the impression support platform having a detachable central portion, the impression support platform sized and shaped so as to be disposed between upper and lower anterior teeth of a patient;
      a dam joined to the impression support platform such that the impression support platform, the dam and the upper anterior teeth and palate of the patient substantially define a mold for forming a dental appliance when the dental device is positioned in a mouth of the patient;
   disposing a sufficient amount of the rapid setting impression material onto the impression support platform to substantially fill the mold;
   positioning the dental device having the rapid setting impression material thereon between the upper and lower anterior teeth of the patient such that the rapid setting of impression material is interposed between the palate and the upper anterior teeth of the patient and the impression support platform;
   disposing the mouth of the patient in a closed condition such that the upper anterior teeth contact the impression support platform and such that the dam substantially contacts the palate of the patient so as to mold the rapid setting impression material into the dental appliance;
   removing the dental device having the dental appliance formed thereon from the mouth of the patient; and
   removing the dental appliance from the dental device such that the detachable central portion detaches from the dental device and remains embedded in the dental appliance.

2. The method of claim 1, wherein in the step of providing the dental device the detachable central portion of the impression support platform includes at least one protuberant to enhance attachment of the detachable central portion to the dental appliance.

3. The method of claim 2, wherein in the step of providing the dental device the at least one protuberant includes an under cut portion so as to further enhance attachment of the detachable central portion to the dental appliance.

4. A dental appliance for positioning a patient's mandible and maxilla in centric relation, formed by the process of:
   providing a rapid setting impression material;
   providing a dental device comprising:
      an impression support platform having a detachable central portion, the impression support platform sized and shaped so as to be disposed between upper and lower anterior teeth of a patient, the impression support platform having an upper surface and a lower surface; and
      a dam joined to the impression support platform such that the impression support platform, the dam and the upper anterior teeth and the palate of the patient substantially enclose and define a mold for a dental appliance when the dental device is positioned in a mouth of the patient;
   disposing the rapid setting impression material onto the upper surface of the impression support platform;
   positioning the dental device having the rapid setting impression material disposed on the upper surface of the impression support platform thereon between the upper and lower anterior teeth of the patient such that the rapid setting impression material is interposed between the palate of the patient and the upper surface of the impression support platform;
   disposing the mouth of the patient in a closed condition such that the lower anterior teeth come into contact with the lower surface of the impression support platform, the upper anterior teeth contact the upper surface of the impression support platform and the dam substantially contacts the palate of the patient thereby forming the mold for the dental appliance;
   maintaining the closed position until the rapid setting impression material substantially solidifies;
   removing the dental device with the dental appliance formed thereon from the mouth of the patient; and
   removing the dental appliance from the dental device such that the detachable central portion detaches from the impression support platform and remains embedded in the dental appliance.

5. The dental appliance of claim 4 wherein, in the step of providing the dental device, the dental device further includes a tab extending from the impression support platform.

6. The dental appliance of claim 5 wherein, in the step of providing the dental device the detachable central portion of the impression support platform includes at least one protuberant for facilitating attachment of the detachable central portion to the dental appliance.

7. The dental appliance of claim 4 wherein, in the step of providing the dental device, an upper surface of the impression support platform of the dental device further includes a convey area capable of creating an air passageway in the dental appliance.

8. The dental appliance of claim 7 wherein, in the step of providing the dental device the dental device further includes a tab extending from the impression support platform.

9. The dental appliance of claim 8 wherein, in the step of providing the dental device the detachable central portion of the impression support platform includes at least one protuberant for facilitating attachment of the detachable central portion to the dental appliance.

10. The dental appliance of claim 9 wherein, in the step of providing the dental device the at least one protuberant includes an under cut portion so as to further enhance attachment of the detachable central portion to the dental appliance.

11. The dental appliance of claim 7 wherein, in the step of providing the dental device the detachable central portion of the impression support platform includes at least one protuberant for facilitating attachment of the detachable central portion to the dental appliance.

12. The dental appliance of claim 4 wherein, in the step of providing the dental device the detachable central portion of the impression support platform includes at least one protuberant for facilitating attachment of the detachable central portion to the dental appliance.

13. A dental device for forming a dental appliance for positioning a patient's mandible and maxilla in centric relation, the dental device comprising:
an impression support platform for supporting a rapid setting impression material, the impression support platform having a detachable central portion that detaches from the dental device and attaches to a dental appliance formed by the dental device, the impression support platform sized and shaped so as to be disposed between upper and lower anterior teeth of a patient; and
a dam to block the rapid setting impression material supported by the impression support platform from going down a patient's throat the impression support platform and the dam sized, shaped and connected such that the impression support platform of the dam and the upper anterior teeth and palate of the patient substantially enclose and define a mold for forming the dental appliance when the dental device is disposed between the upper and lower anterior teeth of the patient.

14. The dental device of claim 13 wherein a detachable central portion of the impression support platform that detaches from the dental device and attaches to the dental appliance when the dental appliance is separated from the dental device includes at least one protuberant to enhance attachment of the detachable central portion to the dental appliance.

15. The dental device of claim 14 wherein the at least one protuberant includes an under cut portion so as to further enhance attachment of the detachable central portion to the dental appliance.

16. A dental device for forming a dental appliance for positioning a patient's mandible and maxilla in centric relation, the dental device comprising:
an impression support platform having a detachable central portion that detaches from the dental device and attaches to a dental appliance formed by the dental device when the dental appliance is separated from the dental device, the impression support platform sized and shaped so as to be disposed between upper and lower anterior teeth of a patient, the impression support platform having an upper surface, a lower surface and a semi-circular outer periphery; and
a dam, having a front surface, a back surface, a semi-circular outer periphery, the dam joined to the impression support platform such that the dam extends in a substantially perpendicular direction from the upper surface of the impression support platform, wherein the upper surface of the impression support platform, the upper surface of the dam and the upper anterior teeth and a palate of the patient substantially enclose and define a mold for forming the dental appliance for positioning the mandible and maxilla of the patient in a centric relation when the dental device is positioned in the mouth of the patient.

17. The dental device of claim 16 wherein a detachable central portion that detaches from the dental device and attaches to the dental appliance when the dental appliance is separated from the dental device of the impression support platform includes at least one protuberant to enhance attachment of the detachable central portion to the dental appliance.

18. The dental device of claim 17 wherein the at least one protuberant includes an under cut portion so as to further enhance attachment of the detachable central portion to the dental appliance.

* * * * *